United States Patent [19]

Dyer et al.

[11] Patent Number: 5,116,328

[45] Date of Patent: May 26, 1992

[54] DIAGNOSTIC KIT FOR THE DETECTION OF ATYPICAL EPITHELIA

[75] Inventors: Dennie W. Dyer, Tiburon; Dennis W. Adair, Suisun City, both of Calif.

[73] Assignee: Oclassen Pharmaceuticals, Inc., San Rafael, Calif.

[21] Appl. No.: 697,908

[22] Filed: May 1, 1991

Related U.S. Application Data

[63] Continuation of Ser. No. 553,791, Jul. 16, 1990.

[51] Int. Cl.$^5$ ............................................. A61M 35/00
[52] U.S. Cl. ................................. 604/289; 604/306; 128/898
[58] Field of Search ................ 128/898; 604/304, 306, 604/289

[56] References Cited

U.S. PATENT DOCUMENTS

| | | | |
|---|---|---|---|
| 3,286,435 | 11/1966 | Weinberger | 15/104.94 |
| 4,252,119 | 2/1981 | Coates | 604/306 |
| 4,643,725 | 2/1987 | Schlasser et al. | 604/306 |

OTHER PUBLICATIONS

Scheffey et al., *Am. J. Obstet. Gynecol.* (1955) 70:886–888.
Scheffey et al., *Obstet. Gynecol.* (1955) 5:294–306.
Schultz and Skelton, *J. Urol.* (1988) 139:777–779.
Sedlacek et al., *Am. J. Obstet. Gynecol.* (1986) 154:494–496.
Shear et al., *J. Am. Acad. Derm.* (1988) 19:372–373.
Townsend, *Colposcopy*, in *Office Gynecology*, Glass ed., (1976: The Williams & Wilkens Co.) pp. 111, 112, 132.
Washington Drug Letter, (Jul. 23, 1990) p. 5.
Wilds, *Obstet. Gynecol.* (1962) 20:645–650.
Baggish, *J. Reprod. Med.* (1982) 27:737–742.
Brillhart, *Indiana Med.* (Sep. 1990), pp. 652–656.
Burke and Mathews, *Colposcopy in Clinical Practice* (1978: F. A. Davis Co.) pp. 16–19, 32–34, 45, 47, 55, 65, 81, 82, 94.
Hinselmann, *Munchener Med. Wochenschr.* (1925) 72:1733.
Meisels et al., *Acta Cytol.* (1977) 21:379–390.
Olson et al., *Obstet. Gynecol.* (1960) 15:372–381.
Pfenninger, *J. Family Prac.* (1989) 29:286–288.
Ries, *Am. J. Obstet. Gynecol.* (1932) 23:393–399.
Rosemburg, *Urology* (1985) 26:554–557.
"Dr. Scholl's Corn Removers with Medicated Disks", commercially available, copyright 1987.

*Primary Examiner*—Randy Shay
*Attorney, Agent, or Firm*—Morrison & Foerster

[57] ABSTRACT

A kit for use in the visualization of genital warts or other atypical epithelia is disclosed. The kit provides a standardized quantity of acetic acid solution on readily available disposable towelettes sealed in a tear-open pouch for use in colposcopy. Methods for visualizing genital warts utilizing the kit are also disclosed.

12 Claims, No Drawings

DIAGNOSTIC KIT FOR THE DETECTION OF ATYPICAL EPITHELIA

This application is a continuation of application Ser. No. 07/553,791, filed Jul. 16, 1990.

BACKGROUND OF THE INVENTION

1. Field of the Invention

This invention relates to the detection of atypical epithelia in human patients. More particularly, it relates to an easily used kit which provides a standardized aqueous acetic acid solution and facilitates a standardized method of application of the acetic acid solution to aid in the detection of atypical epithelia by visual examination or colposcopy.

2. Background Information

Detection of atypical epithelial forms in human patients may often be accomplished by simple visual examination or examination with a magnifying instrument. One such diagnostic procedure utilizes a colposcope in the examination of the male and female genital areas for atypical epithelial forms, in particular genital warts or condyloma. The colposcope is a binocular magnifying optical instrument incorporating a light source for stereoscopic visualization of objects under magnification with direct illumination. The colposcope was originally used in cervical examinations.

Early colposcopic procedures introduced the use of dilute acetic acid (approximately 3%) as an aid in cervical examination. It had been found that wiping the cervix with 3% acetic acid prior to colposcopic examination both cleaned the cervix and brought out detail in the cervical architecture. This procedure reduced epithelial transparency and enhanced the grape-like structure of columnar tissue.

More importantly, it was subsequently found that a 3% aqueous solution of acetic acid caused a change in atypical epithelial forms. Whereas dysplastic and neoplastic epithelia naturally showed no distinction in color from normal tissue, such epithelia took on a well-demarcated whitish hue after the application of acetic acid—termed the positive "aceto-white" response. Stronger acetic acid solutions delineated the atypical tissue more quickly but were irritating to mucous membranes. Weaker solutions required a longer waiting period for the appearance of the demarcation.

These observable changes were transient, developing within one minute after application of acetic acid and fading two to three minutes thereafter. Consequently several applications were often necessary before and during the course of an examination.

Colposcopy is used today both alone and in conjunction with cytologic techniques to determine the presence of neoplasia in the visible portion of the female genital tract. Colposcopy is also used in the diagnosis of penile condyloma in men. Application of acetic acid to the penile area prior to visual examination aids in the detection of atypical epithelia in males in the same way as in females—by the formation of aceto-whites. Examination of males is performed either colposcopically or by unaided visual examination.

A few drawbacks in these diagnostic techniques have prevented them from becoming standard techniques. Interpretation of aceto-white patterns requires accurate description of the architecture and utilizes a terminology many physicians find cumbersome. This drawback is exacerbated by the fact that examining physicians do not use a standardized acetic acid solution in the technique. The commonly used solution is household vinegar, which may vary in acetic acid concentration from 3-5+%. Because acetic acid concentration affects the strength and duration of the aceto-white response, this variation in combination with the need to accurately describe the architecture severely limited the utility of the visual diagnosis of condyloma.

DESCRIPTION OF PRIOR ART

The use of acetic acid in the aid of colposcopy was first described over sixty years ago. H. Hinselman, *Zentralbl. F. Gynak.* (1927) 51:901; H. Hinselman, *Zentralbl. F. Gynak.* (1931) 55:3362; H. Hinselman, *Arch. F. Gynak.* (1933) 156:239. Methods of application of acetic acid to the cervix are described in L. C. Scheffey et al., *Obstet. Gynecol.* (1955) 5:3; and R. H. Glass, *Office Gynecology* (1976: The Williams & Wilkens Co.).

L. Burke and B. E. Mathews, *Colcoscopy in Clinical Practice* (1978: F. A. Davis); and A. Stafl, *Gynecologic Disorders Differential Diagnosis and Therapy* (1982) describe the observed effects and modes of action of acetic acid in colposcopy. The use of acetic acid in colposcopic diagnosis of condyloma in males is described in T. V. Sedlacek et al., *Am. J. Obstet. Gynecol.* (1986) 154:494; R. E. Schultz and H. G. Skelton, *J. Urol.* (1988) 139:777.

STATEMENT OF THE INVENTION

Summary of the Invention

An improvement in the use of acetic acid as an adjunct to visual diagnostic techniques for the detection of genital warts and other atypical epithelia has now been found. In accord with this invention, a healthcare professional is provided with a premeasured effective quantity of a standardized acetic acid solution carried on a premoistened disposable towelette contained in a tear-open sealed pouch.

The present invention gives examining physicians an easily available source of a standardized acetic acid solution for visualization of genital warts and other atypical epithelia. The present invention also provides an easily reproducible method of acetic acid application for visual diagnosis. The reproducibility of the acetic acid concentration and method of application makes visual diagnosis of genital warts a more informative and useful technique.

In one aspect, this invention provides a kit for use in the visualization of genital warts and other atypical epithelia. The kit includes a towelette carrying a premeasured standard volume of a standardized concentration acetic acid solution. The towelette is sealed in a frangible containing pouch from which it can be removed for use. The towelette fibers are bonded, and the containing pouch is laminated to resist acetic acid attack. In preferred embodiments, the acetic acid is from 2.5% to 6% by volume in concentration. The towelette fibers are bonded with an ethylene-vinyl acetate copolymer, and the containing pouch is laminated on the inside with polyethylene.

In another aspect of this invention, a method for visualization of genital warts in a patient is provided, wherein a kit having a towelette soaked in a standardized dilute acetic acid solution and sealed in a frangible containing pouch is obtained, the pouch is opened, and the towelette is removed and applied to the patient's genital area.

DETAILED DESCRIPTION OF THE INVENTION

The condyloma diagnostic kit provided by the present invention is made up of an acetic acid solution carried by a disposable towelette contained within a sealed but openable liquid-impermeable pouch. In this Detailed Description of the Invention section these components will be discussed in the following order:
A. The Acetic Acid Solution
B. The Application Towelette
C. The Containing Pouch
D. Methods of Use
E. Examples

A. The Acetic Acid Solution

The acetic acid solutions employed in this invention aid in the detection of condyloma by the formation of "aceto-whites." Acetic acid in the range of 2-6% is known in the art as effective in aceto-white formation. The acetic acid solutions employed in this invention are aqueous solutions and are in the range of 2-6% acetic acid. Preferred solutions contain from 3% to 5% acetic acid.

The reaction of acetic acid to make condyloma visible varies significantly depending on the acetic acid concentration. With solutions below the lower end of the 2-6% range, the development of aceto-whites takes too long and the condylomata are often not as visible as desired. Solutions at or beyond the higher end of this range produce a more rapid reaction, but also tend to be irritating to mucous membranes, especially after repeated applications.

Variation in acetic acid concentration among patient diagnostic examinations results in inexactitude in the diagnoses due to irreproducibility and lack of a basis for comparison. The acetic acid solutions provided in this invention typically are standardized to an exact reproducible percentage to provide reproducibility and a standard of comparison among patients and physicians. In two preferred embodiments of this invention, the acetic acid concentrations are 3% and 5%. These levels are selected primarily because they are convenient.

The amount of acetic acid carried on the towelette is relatively substantial—that is, more than 1 or 2 cc. The amount selected should be adequate to reproducibly saturate the carrier towelette and permit a reproducible diagnosis but not so great as to drip off of the towelette in use. Thus the amount will depend at least in part on the dimensions and carrying capacity of the towelette. Good results are obtained with volumes of acetic acid in the range of about 10 to about 30 cc, and especially 15 to 25 cc.

B. The Application Towelette

An applicating towelette is employed in this invention. In use, it is permeated with the acetic acid solution. Also in use, the towelette may remain in contact with the acetic acid for a prolonged period of time depending upon the shelf-life of the product of up to several months or years. Suitable materials of construction for the towelette are those which retain their physical integrity over this prolonged period. In this setting, it must be kept in mind that acetic acid is corrosive and a relatively strong acid. Prolonged exposure to a strong and corrosive acid can lead to breakdown of many materials which might otherwise be chosen. The material of fabrication should also be relatively hydrophilic so as to absorb and not repel the aqueous acetic acid solution. This property is needed to assure that the towelette will take up and hold the volumes of acetic acid which are required in this kit. Any material that meets these criteria and is safe for use in contact with the genitalia in the setting of the invention may be used and is included within the scope of the present invention. The material will typically be fibrous and may be in the form of a felt, a woven fabric or a compressed and optionally patterned felt-like material such as paper.

These selection criteria can serve to eliminate some otherwise likely towelette candidates. For example, a simple untreated paper towelette or a simple untreated sterile cotton gauze will be broken down by prolonged contact with acetic acid. Similarly, some durable fiber materials such as fiberglass, synthetic polymer fiber fabrics, etc., are not very hydrophilic and thus do not take up and hold the acetic acid suitably.

Good results may be attained using materials which include a hydrophilic natural or synthetic fiber substrate and an overcoating or sizing of a synthetic hydrophilic polymer binder or sizing. Such materials include cellulosic fiber substrates such as paper, cotton or the like with a polymeric binder such as ethylene-vinyl acetate. Typical amounts of binder are from about 0.5 to about 5% by weight basis total dry towelette.

A typical application towelette is from about 15 to 25 cm in length and width, and about 0.5 to 1.5 mm in thickness.

C. The Containing Pouch

A containing pouch is provided to contain the acetic acid solution and the acetic acid-permeated towelette. The pouch is fabricated to enclose the solution and towelette. It is made of a material which is liquid impermeable and resistant to attack by the acetic acid solution.

The pouch may be made of any acetic acid-impermeable and resistant material that can be sealed into an enclosing configuration and that can be opened by cutting or tearing. Plastic films such as poly(ethylene), poly(propylene), poly(ester) such as poly(ethylene terephthalate), saran polymers, blends thereof and the like can be used. Such materials can work well but can at times by themselves be somewhat too fragile. Preferred materials are outer foil/inner plastic film laminates and paper/foil/plastic laminates. These materials are available in sterile drug-compatible forms such as those materials sold by Nice-Pak Products, Inc. as Web NP-3216 (1-mil) (a laminate of 26# paper/7# LDPE/0.00035" foil/adhesive/48 g PET/15# Surlyn 1652); and Web NP 3400 (a paper/foil/plastic film made up of 25# CIS paper/7# LDPE/0.00035" foil/107 Scotchpak (PET/LDPE)).

Such materials can be laminated into pouches using heat sealing or added adhesive.

D. Methods of Use

The diagnostic kit provided in this invention is a prepackaged kit having a towelette carrying a premeasured volume of a standardized acetic acid solution and sealed in a frangible pouch. The pouch is easily opened and disposed of after use. The standardized acetic acid solution allows easy comparison and reproducible results.

In the methods of this invention, an examining physician or other qualified personnel, having a patient ready for visual diagnostic examination for the presence of genital warts, obtains the prepackaged kit, opens it and removes the towelette carrying the standardized acetic acid solution. The towelette is then used to transfer acetic acid to the area to be examined.

In female patients, the towelette may be placed on the external genital area and be allowed to soak for a limited period of time. Alternatively, the towelette may be used to swab or otherwise apply the solution. If the towelette had been folded inside the pouch, it may be fully opened, partially opened, or remain in a folded state when used.

In male patients, the towelette may be fully opened and wrapped around the penis or the scrotum or both and allowed to soak for a limited period of time. Alternatively, the towelette may be used as a swab or applicator as for female patients.

When the towelette is allowed to soak the genital area, the soaking period may last up to about 10 minutes. In a preferred embodiment of this invention, the soaking period is from about 3 to about 10 minutes. In the most preferred embodiment of this invention, the soaking period is about 5 minutes. After the application of the acid solution, the patient is examined for the appearance of aceto-whites as an indication of condyloma.

After the towelette has been used to wrap, soak, or apply the acetic acid solution, it, as well as the enclosing pouch, may be discarded.

This invention will be shown by the following Example. It is provided to illustrate one mode of practicing the invention but is not to be interpreted as limiting its scope.

E. Example

A white, non-embossed airlay single-ply fabric made of wood pulp fiber bonded with an ethylene-vinyl acetate binder was obtained from Nice-Pak Products, Inc. The material was white in color, free of contamination, clump and foreign material. It was 42#/ream in weight and 46 mils in thickness (1.2 mm). It was acid resistant with a minimum wet tensile strength of 1250 grams/3 inch in the wet MD test. The material was microbiologically clean, containing $\leq 100$ colony-forming units of aerobic species per 7.75"×7.75" area and no colony-forming units of *Staphylococcus aureus, E. coli, Pseudomonas aeruginosa* and molds and yeasts.

The material was cut into towelette size pieces, selected at 7.75"×7.75". (Larger of smaller pieces could have been used, if desired.)

The towelette was then folded in each direction into an about 1½"×2½" rectangle. This rectangle was placed on a sheet of Nice-Pak Web NP #3400 paper/foil/-Scotchpak packaging material which was larger than the folded towelette.

The NP #3400 material is a commercially available product which is a 25# paper/7# low-density polyethylene/0.00035" foil/0.07 Scotchpak polyethylene terephthalate/low-density polyethylene film laminate. The NP #3400 is placed paper side down with the plastic side up and the towelette on the plastic side.

Next, 20 ml of a 5% aqueous solution of acetic acid was added to the folded towelette so as to saturate it with acetic acid. Then a second sheet of NP #3400 was laid plastic side down over the folded towelette. The two sheets of NP #3400 were then pressed together and heat-sealed to one another around the perimeter of the folded towelette, thus enclosing the towelette in a sealed, liquid-tight pouch.

The pouch was then trimmed to shape. If desired, a label could be applied to the outside of the pouch or imprinted on the outside of the pouch.

One concern regarding the pouches was how they would stand up in storage. A bacterial challenge was conducted in which a sample towelette with acetic acid loading was inoculated with *E. coli, P. aeruginosa, S. aureus,* yeast and mold, sealed in a pouch, and then stored at ambient conditions for 35 days. None of the inoculated organisms were detectable in the towelette at that time. The kit is predicted to have a shelf life of at least 18 months.

The pouch was convenient to store and easily torn open for use. When opened, the towelette was moist but intact. It was a convenient size and could be used to diagnose genital warts on men and women alike.

We claim:

1. A kit for use in the visualization of atypical epithelia comprising:
   a tear-open, liquid-impermeable sealed pouch made up of two flexible sheets, the sheets each having an inner surface which is resistant to aqueous acetic acid and an outer surface, the two sheets joined to one another at their peripheries, thereby defining an inner chamber;
   an applicating towelette formed of an acetic acid-resistant, hydrophilic substrate residing in the inner chamber; and
   an effective atypical epithelia-visualizing amount of aqueous acetic acid solution residing in the inner chamber and permeating the applicating towelette,
   wherein the substrate from which the applicating towelette is formed comprises pulp fiber with an acetic acid-resistant polymeric binder.

2. The kit of claim 1 wherein the acetic acid-resistant polymeric binder comprises an ethylene-vinyl acetate copolymer.

3. The kit of claim 2 wherein the aqueous acetic acid solution contains 3 to 5% acetic acid.

4. The kit of claim 1 wherein the atypical epithelia to be visualized are genital warts, and further wherein the effective atypical epithelia-visualizing amount of aqueous acetic acid solution is an effective wart-visualizing amount.

5. A kit for use in the visualization of atypical epithelia comprising:
   a tear-open, liquid-impermeable sealed pouch made up of two flexible sheets, the sheets each having an inner surface which is resistant to aqueous acetic acid and an outer surface, the two sheets joined to one another at their peripheries, thereby defining an inner chamber;
   an applicating towelette formed of an acetic acid-resistant, hydrophilic substrate residing in the inner chamber; and
   an effective atypical epithelia-visualizing amount of aqueous acetic acid solution residing in the inner chamber and permeating the applicating towelette,
   wherein the two sheets each comprise a layer of aluminum foil laminated with a layer of an acid-resistant polymer on the inner surfaces.

6. The kit of claim 5 wherein the acid-resistant polymer is selected from the group of polyethylene, polypropylene, polyester and mixtures thereof.

7. The kit of claim 5 wherein the atypical epithelia to be visualized are genital warts, and further wherein the effective atypical epithelia-visualizing amount of aqueous acetic acid solution is an effective wart-visualizing amount.

8. A kit for use in the visualization of atypical epithelia comprising:
   - a tear-open, liquid-impermeable sealed pouch made up of two flexible sheets, the sheets each having an inner surface which is resistant to aqueous acetic acid and an outer surface, the two sheets joined to one another at their peripheries, thereby defining an inner chamber;
   - an applicating towelette formed of an acetic acid-resistant, hydrophilic substrate residing in the inner chamber; and
   - an effective atypical epithelia-visualizing amount of aqueous acetic acid solution residing in the inner chamber and permeating the applicating towelette,
   - wherein the two sheets each comprise a paper/foil/plastic laminate wherein the plastic layer defines the inner chamber and the plastic is selected from polyethylene, polypropylene, polyethylene terephthalate and mixtures thereof.

9. The kit of claim 8 wherein the atypical epithelia to be visualized are genital warts, and further wherein the effective atypical epithelia-visualizing amount of aqueous acetic acid solution is an effective wart-visualizing amount.

10. A method for visualizing atypical epithelia on an epithelial area of a patient comprising the following steps:
   (a) obtaining a kit comprising a tear-open, liquid-impermeable sealed pouch made up of two flexible sheets, the sheets each having an inner surface which is resistant to acetic acid and an outer surface, said sheets joined to one another at their peripheries, thereby defining an inner chamber;
   an applicating towelette formed of a substrate comprising pulp fiber with an acetic acid-resistant polymeric binder and residing in the inner chamber; and
   an effective atypical epithelia-visualizing amount of aqueous acetic acid solution residing in the inner chamber and permeating the applicating towelette;
   (b) opening the sealed punch and removing the applicating towelette and associated acetic acid solution from the inner chamber;
   (c) applying the towelette to the patient's epithelial area, thereby concomitantly applying acetic acid to the area for an effective time period adequate to generate aceto-whites with any atypical epithelia; and
   (d) examining the area for aceto-whites, thereby visualizing the atypical epithelia.

11. The method of claim 10 wherein in step (a) the aqueous solution contains 2 to 6% acetic acid.

12. The method of claim 10 wherein the atypical epithelia to be visualized are genital warts, and further wherein the effective atypical epithelia-visualizing amount of aqueous acetic acid solution is an effective wart-visualizing amount.

* * * * *